United States Patent
Kumagai

(10) Patent No.: US 8,211,718 B2
(45) Date of Patent: Jul. 3, 2012

(54) SEMICONDUCTOR DEVICE AND METHOD OF VISUAL INSPECTION AND APPARATUS FOR VISUAL INSPECTION

(75) Inventor: Hokuto Kumagai, Kanagawa (JP)

(73) Assignee: Renesas Electronics Corporation, Kanagawa (JP)

( * ) Notice: Subject to any disclaimer, the term of this patent is extended or adjusted under 35 U.S.C. 154(b) by 0 days.

(21) Appl. No.: 13/030,717

(22) Filed: Feb. 18, 2011

(65) Prior Publication Data

US 2011/0141268 A1    Jun. 16, 2011

Related U.S. Application Data

(62) Division of application No. 12/040,950, filed on Mar. 3, 2008, now Pat. No. 7,919,869.

(30) Foreign Application Priority Data

Mar. 1, 2007    (JP) .................................. 2007-051704

(51) Int. Cl.
*H01L 21/66* (2006.01)
(52) U.S. Cl. ............. 438/14; 438/18; 438/622; 438/637
(58) Field of Classification Search .................. 438/118, 438/622, 625, 637, 11, 14; 257/774, E23.01
See application file for complete search history.

(56) References Cited

U.S. PATENT DOCUMENTS

| 2004/0084777 A1* | 5/2004 | Yamanoue et al. ........... 257/758 |
| 2005/0269702 A1 | 12/2005 | Otsuka |
| 2007/0178691 A1* | 8/2007 | Richter et al. ................ 438/625 |

FOREIGN PATENT DOCUMENTS

| JP | 2003-727592 | * 10/2003 |
| JP | 2005260059 | 9/2005 |
| JP | 2005-277338 | 10/2005 |
| WO | 2004-097917 | 11/2004 |

OTHER PUBLICATIONS

Japanese Official Action—2007-051704—Apr. 17, 2012.

* cited by examiner

*Primary Examiner* — Thinh T Nguyen
(74) *Attorney, Agent, or Firm* — Young & Thompson

(57) ABSTRACT

A semiconductor device having the structure, which is adopted for the highly precise visual inspection with a lower cost, is achieved. A semiconductor device is a semiconductor device having a region for forming an electric circuit, and includes seal rings provided in an interconnect layer and surrounding the region for forming an electric circuit, and a dummy metal via provided in the interconnect layer and located outside of the seal rings. In a cross section perpendicular to an elongating direction of the seal ring, the width of the dummy metal via is smaller than the width of the seal ring.

7 Claims, 13 Drawing Sheets

SEMICONDUCTOR DEVICE AND METHOD OF VISUAL INSPECTION AND APPARATUS FOR VISUAL INSPECTION

This application is based on Japanese patent application No. 2007-51,704, the content of which is incorporated hereinto by reference. This Application is a divisional application of and claims priority to application Ser. No. 12/040,950 (filed on Mar. 3, 2008), now U.S. Pat. No. 7,919,869.

BACKGROUND

1. Technical Field

The present invention relates to a semiconductor device and a method and an apparatus for inspecting an appearance thereof.

2. Related Art

Sophistications and diversifications of semiconductor devices in recent years promote uses of various types of materials in diffusion processes for semiconductor wafers. New materials, which are newly employed for such processes, include films having lower adhesiveness or lower mechanical strength, and such materials may cause problems, in which mechanical shocks during wafer-dicing process create cracks between interconnect layers, leading to a progressing peeling-off of such material toward chips. Such problem becomes particularly considerable in dicing processes for semiconductor wafers that employ insulating films called "low-K film" having lower specific dielectric constant than that of $SiO_2$ film.

When an assembly of chips having cracks therein is conducted, the cracks become worse by a heat stress in the assemble process to cause defects of flaking-off. Therefore, a precise detection of cracks in wafers after the dicing process greatly affects a reliability of the product.

In addition to above, related prior art documents for the present invention include Japanese Patent Laid-Open No. 2005-260,059 and Japanese Patent Laid-Open No. 2005-277, 338.

In the actual manufacturing processes, a human visual inspection for an appearance of products or an automatic visual inspection with devices is conducted by employing a metaloscope or a stereomicroscope. In such case, focus is taken to a surface of a wafer.

When a crack is grown toward Z-direction (direction to be perpendicular to the surface of the substrate), the cracked piece is considerably inclined. Otherwise, the growth of the crack all the way eventually creates a chipped piece. As shown in FIG. 8, even if a polyimide film 203 is disposed above the wafer, if a crack 110 is proceeded all the way in Z direction, the polyimide film 203 is pushed up and is bent, as shown in plan view of FIG. 9. This reveals itself in a form of a discoloration 111 in its appearance, and thus, fortunately, a crack can be easily detected. In addition to above, in FIG. 8, the interconnect layer 202 and the polyimide film 203 are sequentially stacked on the silicon substrate 201.

However, when the crack is mainly grown only along x-y directions (direction along the surface of the substrate), the resultant step is relatively smaller of a height of less than several microns, and in such case, an identification of such crack is difficult, even if an observation is made with a precise focusing. Further, as shown in FIG. 10, if metal vias 112 (guard rings) are embedded in a portion, which is flaked-off, an identification of such crack can be achieved by an observation of the cross section, since a deformation 113 is occurred in that location. However, since the observation of the appearance is carried out from the above with a certain focusing, an obtained result of appearance 114 indicates no positional change of the metal or a slight bending of the inner metal (FIG. 11), and therefore it is very difficult to know a presence of a flaking-off in the wafer.

Since a manual observation, which depends upon a visual acuity of an operator, is carried out with a relatively lower accuracy, a detection of a flaked-off portion growing only along a direction of the surface of the substrate may not be excluded in the results of the observation, and thus a diffusion of the defects may be easily caused.

In general, in the case of directly and visually observing the cracks in the interconnect surface of the semiconductor chip, metaloscopes or stereomicroscopes are not suitable for sufficiently detecting the cracks, due to their lower magnifications, and therefore a scanning electron microscope (SEM) with higher magnification is necessary. However, an automation of the device for the visual inspection of the semiconductor chips in the mass production process by employing the SEM that requires an ultra-high-vacuum chamber is difficult to be achieved and provides increased manufacturing costs.

SUMMARY

According to one aspect of the present invention, there is provided a semiconductor device having a region for forming an electric circuit, comprising: a guard ring, provided in an interconnect layer, and surrounding said region for forming the electric circuit; and a dummy metal via, provided in said interconnect layer and located outside of said guard ring; wherein a width of said dummy metal via is smaller than a width of said guard ring in a cross section that is perpendicular to a direction of an elongation of said guard ring.

In this semiconductor device, a dummy metal via having smaller width than the width of the guard ring is provided outside the guard ring. When a crack is grown, the dummy metal via is bent, and is displaced toward the direction along the surface of the substrate. Therefore, by identifying an occurrence of such displacement, the crack can be indirectly detected. Here, the identification of the above-described displacement can be carried out with an apparatus that requires a lower cost, as compared with the case of directly identifying the crack. Thus, for the semiconductor device having such structure, a highly precise visual inspection can be conducted with lower cost.

According to the present invention, a semiconductor device having the structure, which is adopted for the highly precise visual inspection with a lower cost, and a method an apparatus for inspecting the appearance thereof is achieved.

BRIEF DESCRIPTION OF THE DRAWINGS

The above and other objects, advantages and features of the present invention will be more apparent from the following description of certain preferred embodiments taken in conjunction with the accompanying drawings, in which.

DETAILED DESCRIPTION

The invention will be now described herein with reference to illustrative embodiments. Those skilled in the art will recognize that many alternative embodiments can be accomplished using the teachings of the present invention and that the invention is not limited to the embodiments illustrated for explanatory purposed.

Exemplary implementations according to the present invention will be described in reference to the annexed figures. In all figures, an identical numeral is assigned to an element commonly appeared in the figures, and the detailed description thereof will not be repeated.

Figure 1:
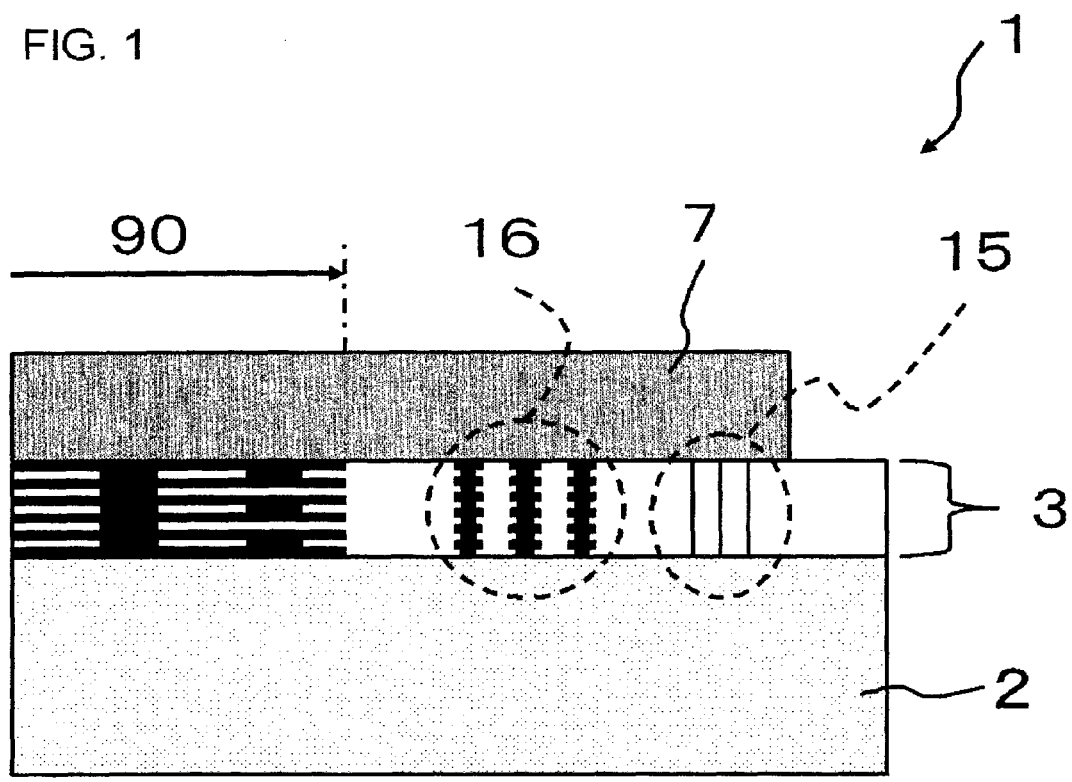
FIG. 1 is a cross-sectional view, illustrating an exemplary implementation of a semiconductor device according to the present invention.
Figure 2:
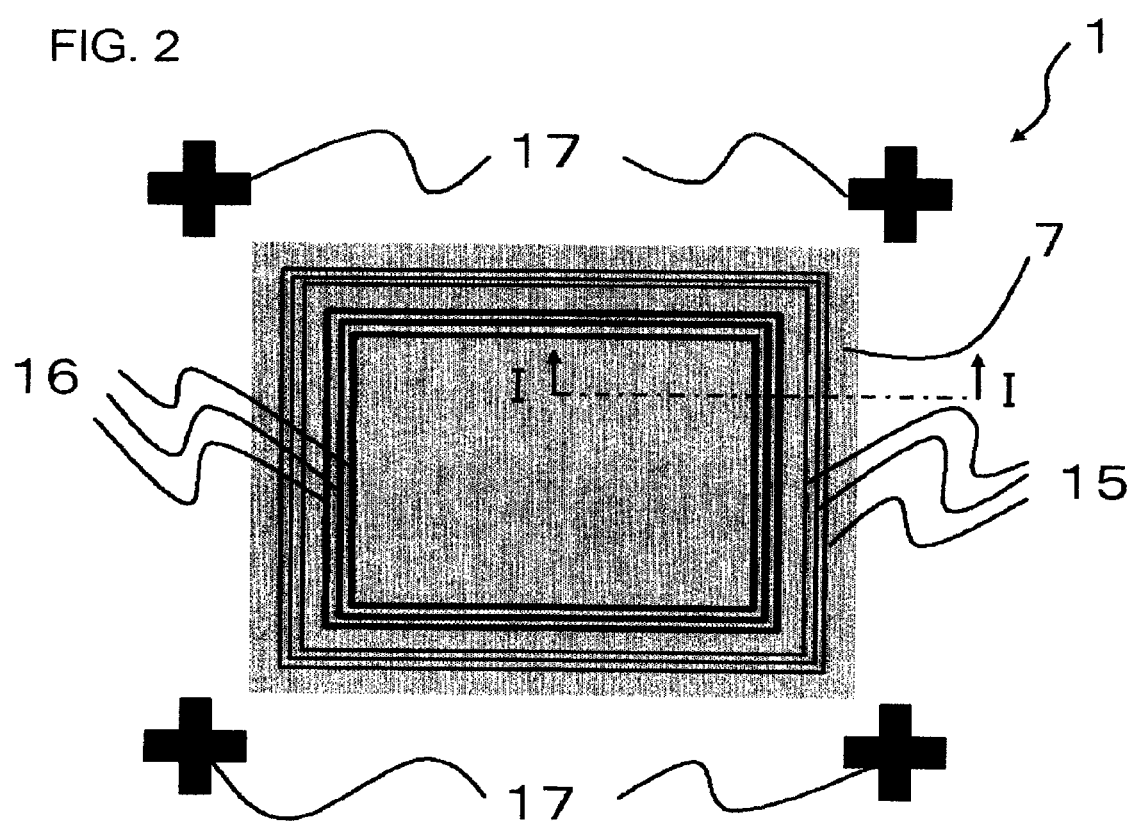
FIG. 2 is a plan view, illustrating an exemplary implementation of a semiconductor device according to the present invention.

FIG. 1 and FIG. 2 are a cross-sectional view and a plan view, respectively, illustrating an embodiment of a semiconductor device according to the present invention. A cross section along line I-I of FIG. 2 corresponds to FIG. 1. A semiconductor device 1 is a semiconductor device having a region 90 for forming an electric circuit, and includes seal rings 16 (guard rings) provided in an interconnect layer 3 and surrounding the region 90 for forming an electric circuit, and a dummy metal via 15 provided in the interconnect layer 3 and located outside of the seal rings 16. In addition to above, the "dummy metal via" appeared in this Specification is a dummy metal via, a presence of which provides no influence over the the circuit architecture of the semiconductor device 1.

Dummy metal vias 15 are arranged between the seal rings 16 and scribe lines. In FIG. 2, cross marks 17 are indicated in intersecting positions with the scribe lines. No polyimide film 7 is provided on the scribe line.

The interconnect layer 3 includes a low-K (low-dielectric constant) film. This interconnect layer 3 is formed on the substrate 2. In the present embodiment, the semiconductor substrate 2 is a silicon substrate. Further, a polyimide film 7 is provided over the interconnect layer 3. While the exemplary implementation provided with the dummy metal via 15 on the polyimide film 7 is illustrated in this embodiment, the polyimide film 7 is not necessary to be disposed on the dummy metal via 15.

In a cross section (equivalent to a cross section shown in FIG. 1) perpendicular to an elongating direction of the seal ring 16 (direction to be perpendicular to the plane of FIG. 1), the width of the dummy metal via 15 is smaller than the width of the seal ring 16. More specifically, a length of the dummy metal via 15 along a transverse direction in FIG. 1 is smaller than that of the seal ring 16. Smaller width of the dummy metal via 15 as described above provides higher accuracy in detecting the cracks. The upper limit of the width of the dummy metal via 15 may be distinctly smaller than the seal ring, for example, 5 μm. The lower limit thereof may be a minimum width, which is a limited value for the manufacturing process such as a lithographic process or the like. Further, the widths may not be identical in all of the interconnect layers, and for example, a configuration having an increased width toward the above of the via may also be employed. Further, it is not necessary to provide the dummy metal vias 15 in all the interconnect layers, and for example, the dummy metal via 15 may be disposed only in the underlying interconnect layer corresponding to a low-K film.

The dummy metal via 15 is provided over the entire peripheral of the region 90 for forming the electric circuit 90, as shown in FIG. 2. Further, a plurality (three vias in the present embodiment) of dummy metal vias 15 are provided. When a plurality of dummy metal vias 15 are disposed in such way, a progress of cracks can be more visually evaluated. However, one dummy metal via 15 may be sufficient, and even in such case, sufficient advantageous effects can be obtained.

The dummy metal via 15 preferably has higher aspect ratio as possible. Higher aspect ratio provides higher accuracy for detecting cracks. Here, the aspect ratio of the dummy metal via 15 is defined as ratio of height of the dummy metal via 15 (length of dummy metal via 15 along longitudinal direction in FIG. 1) to the above-described width.

The dummy metal via 15 has a damascene structure in the present embodiment. More specifically, the dummy metal via 15 is formed by a damascene process. Such damascene process may be a single damascene process or a dual damascene process. In addition to above, while the cross-section geometry of the dummy metal via 15 may be a rectangular geometry, a trapezoid may also be employed if a rectangular geometry is difficult to be produced on a process-related reason. Further, aluminum (Al), copper (Cu) or tungsten (W) may be employed for a material of the dummy metal via 15.

Figure 3:
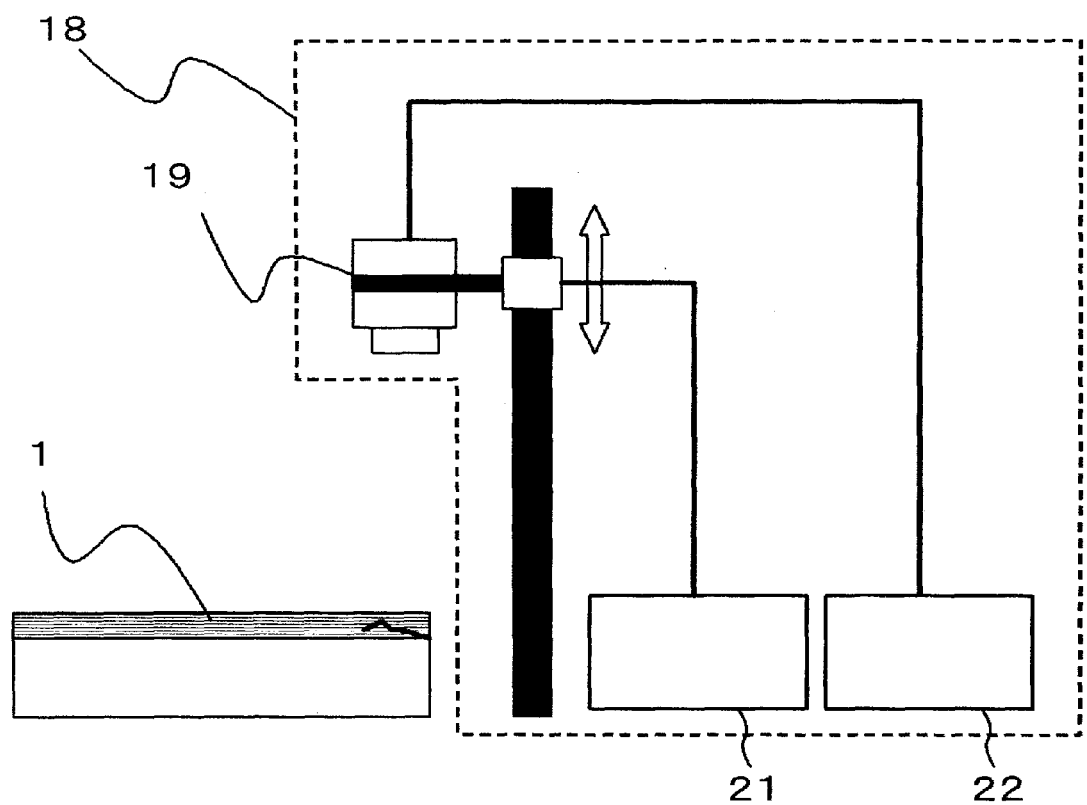
FIG. 3 is a cross-sectional view, illustrating an exemplary implementation of a visual inspection apparatus according to the present invention.

FIG. 3 is a cross-sectional view, illustrating an embodiment of a visual inspection apparatus according to the present invention. A visual inspection apparatus 18 is an apparatus that is employed in inspecting an appearance of a semiconductor device 1, and includes an identification unit that is capable of identifying a displacement of the dummy metal via 15. Such identification unit provides an identification of a displacement of the dummy metal via 15 by an omnifocal photographic process from above the semiconductor device 1.

In the present embodiment, the above-described identification unit includes a camera 19 that is capable of picking up an image of the dummy metal via 15; a changing unit 21 that is capable of changing a distance between the camera 19 and the semiconductor device 21; and an image processing unit 22 that is capable of generating an omnifocal image of the dummy metal via 15 from images of the dummy metal via 15, which are picked up with the camera 19 by a condition of a plurality of the distances of different values changed by the changing unit 21. The changing unit 21 changes the above-described distance by displacing the camera 19 along Z-direction (longitudinal direction in FIG. 3).

A combination of the camera 19 and the changing unit 21 may be a combination of a micro scope camera and a Z-axis-mobable unit, or may be a combination of a microscope and a Z-axis-controlling unit. The camera 19 may preferably be capable of magnifying the image by about 50-fold to 200-fold.

An example of an operation of the visual inspection apparatus 18 will be described as an exemplary implementation of a visual inspection process according to the present invention. Such process is, in general, a process for inspecting an appearance of the semiconductor device 1, and includes identifying a displacement of the dummy metal via 15. An identification of a displacement of the dummy metal via 15 is achieved by an omnifocal photography process viewed from above the semiconductor device 1.

Figure 4:
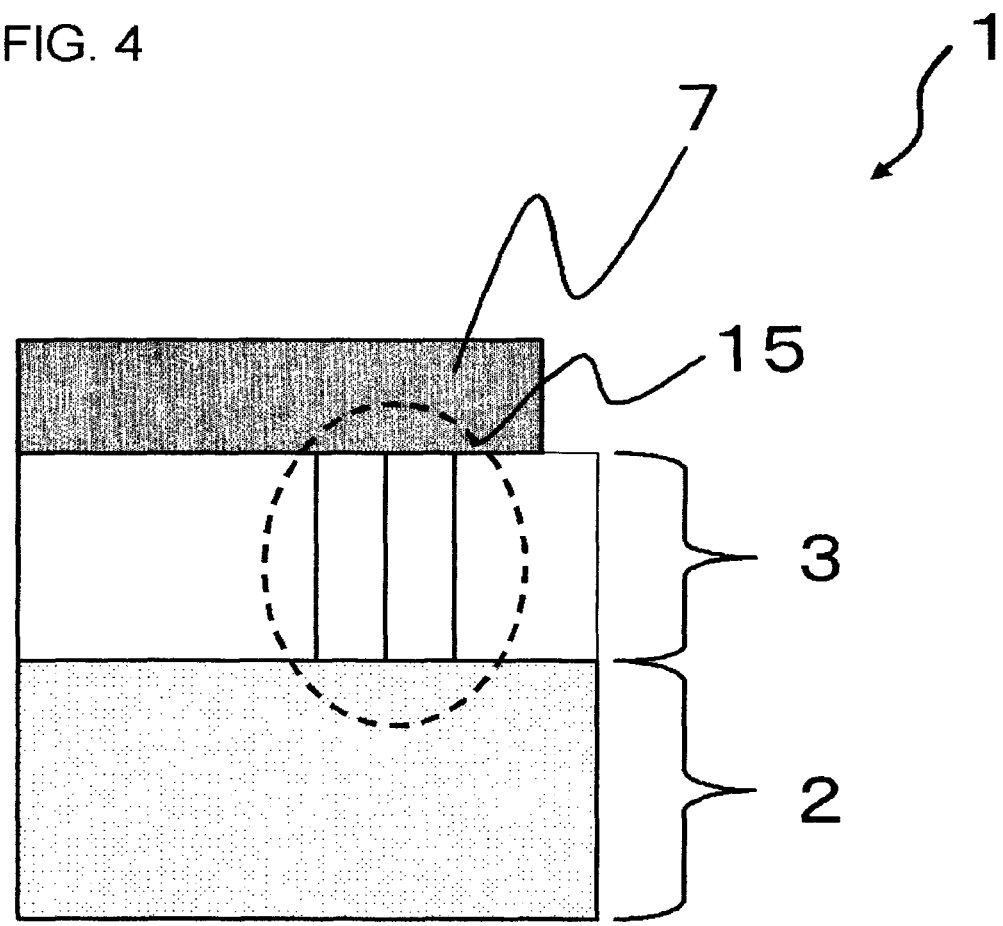
FIG. 4 is a cross-sectional view, useful in describing an exemplary implementation of a process for visual inspection according to the present invention.
Figure 5:
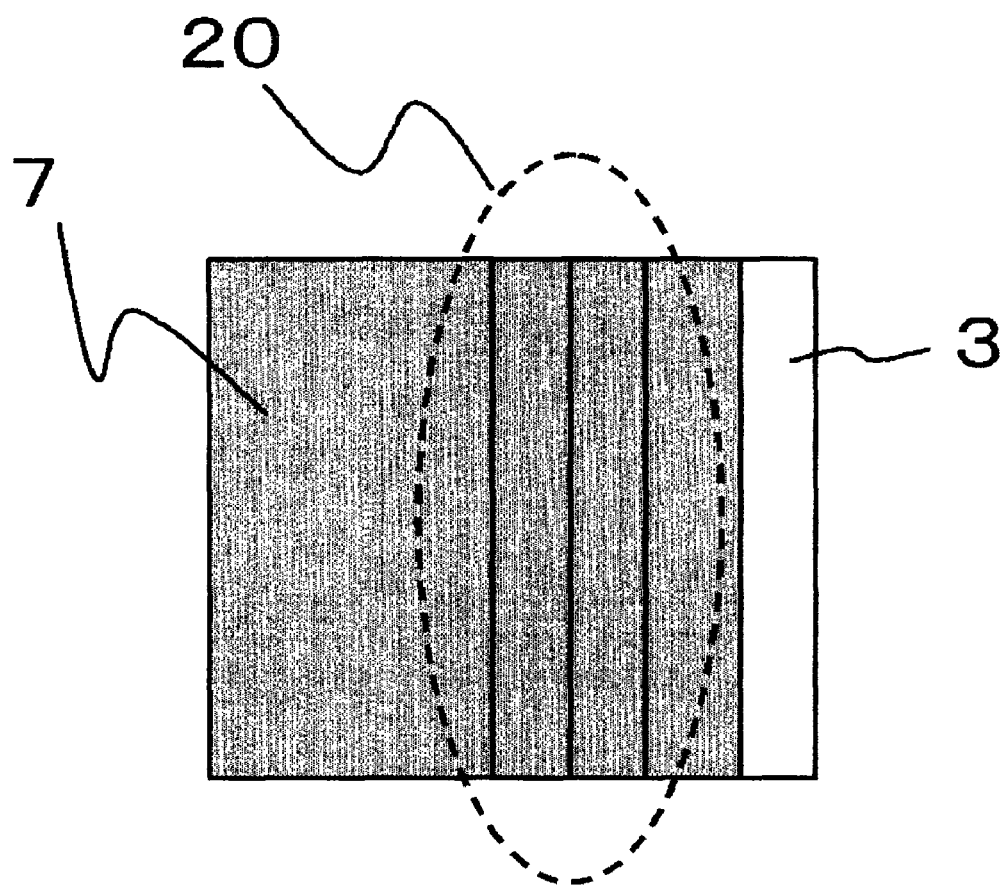
FIG. 5 is a plan view, useful in describing an exemplary implementation of a process for visual inspection according to the present invention.

More specifically, the semiconductor device 1 is first set in a certain position after finishing a dicing process. Next, a focus is adjusted on the vicinity of the scribe line of the semiconductor device 1, and then images are picked up while moving the camera 19 along Z-direction at a minimum moving rate by employing the changing unit 21 to form an omnifocal image. If no crack is found in the interconnect layer 3 of the semiconductor device 1 as shown in FIG. 4, the omnifocal image 20 of dummy metal via 15 is observed without any curvature as shown in FIG. 5.

Figure 6:
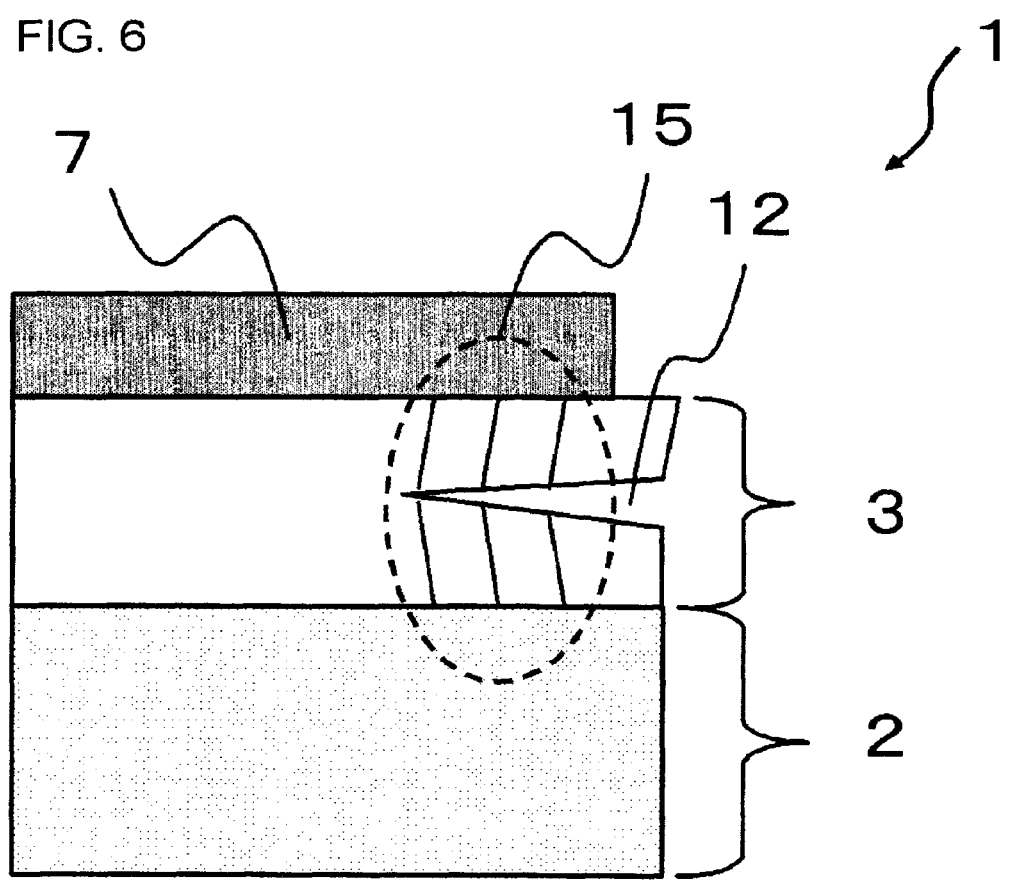
FIG. 6 a cross-sectional view, useful in describing an exemplary implementation of a process for visual inspection according to the present invention.
Figure 7:
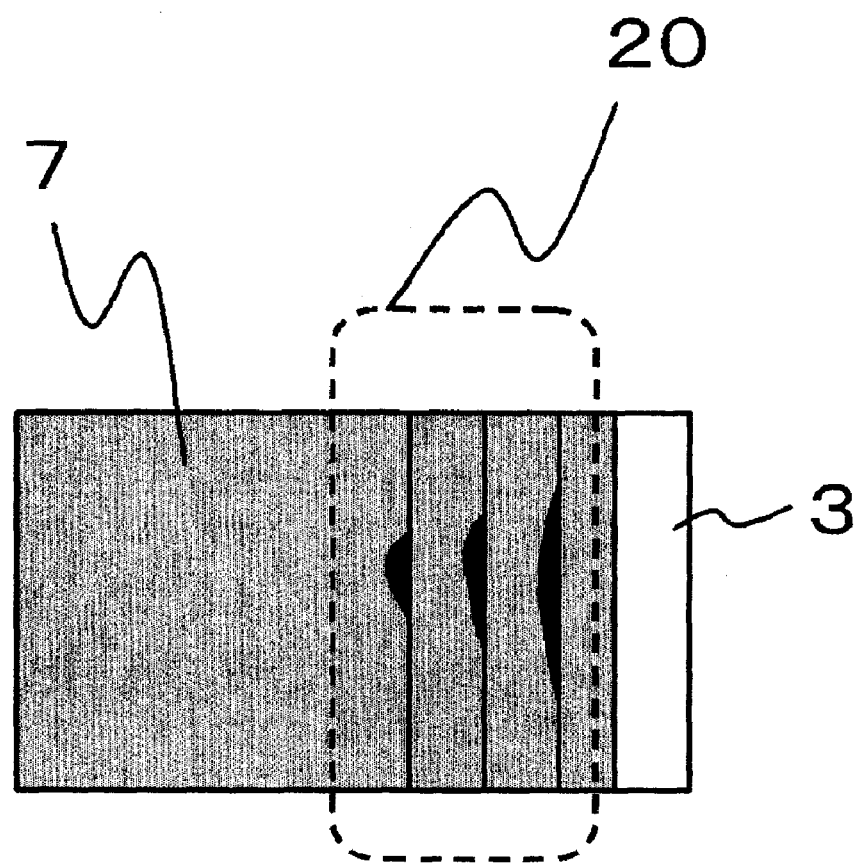
FIG. 7 is a plan view, useful in describing an exemplary implementation of a process for visual inspection according to the present invention.
Figure 8:
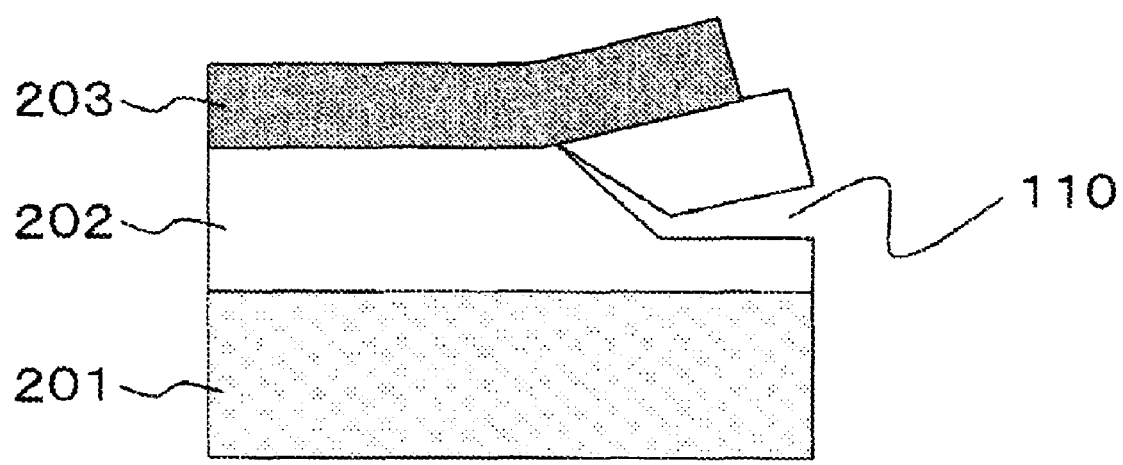
FIG. 8 is a cross-sectional view for describing a problem arisen in the conventional technology.
Figure 9:
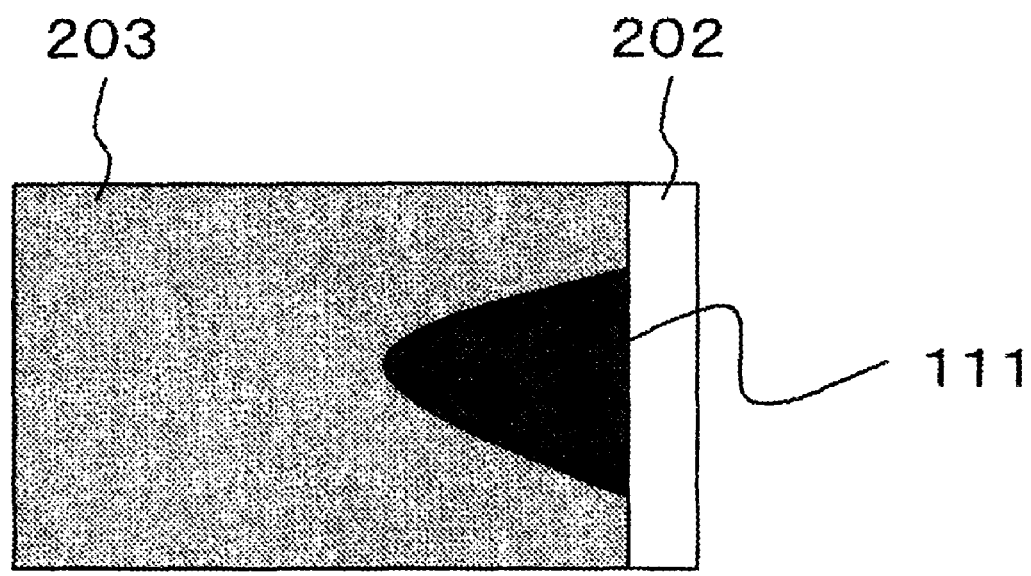
FIG. 9 is a plan view for describing a problem arisen in the conventional technology.
Figure 10:
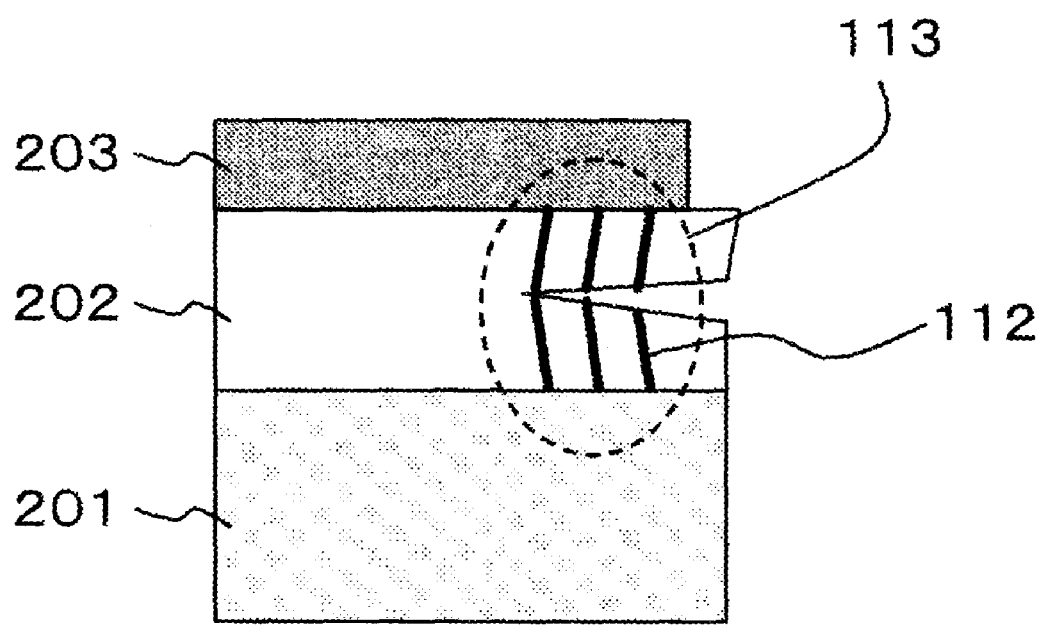
FIG. 10 is a cross-sectional view for describing a problem arisen in the conventional technology.
Figure 11:
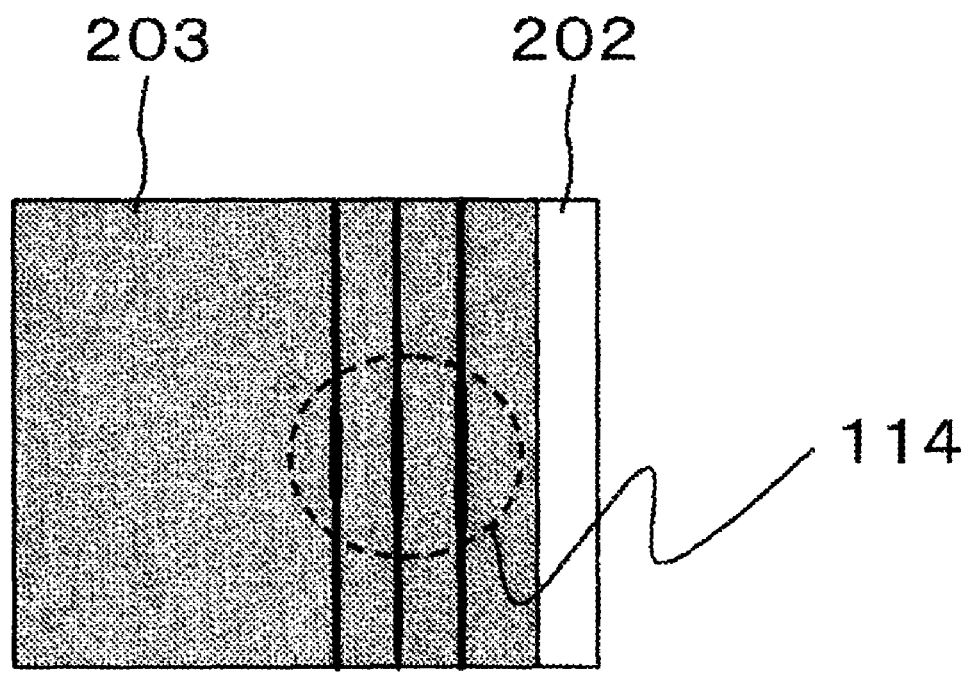
FIG. 11 is a plan view for describing a problem arisen in the conventional technology.

On the other hand, a case having a crack 12 in the interconnect layer 3, which is grown in the direction along the surface of the semiconductor substrate 2 will be considered as shown in FIG. 6. When an omnifocal image of portions including bent sections of the dummy metal via 15 is picked up from above in such case, corresponding portions of the omnifocal image 20 of the dummy metal via 15 is observed to be curved, as shown in FIG. 7. This allows knowing a presence and a growth of a crack.

Advantageous effects obtainable by employing the configuration of the present embodiment will be described. In the semiconductor device 1, a dummy metal via 15 having smaller width than the width of the guard ring 16 is provided outside the guard ring 16. When a crack is grown, the dummy metal via 15 is bent, and is displaced toward the direction along the surface of the substrate 2. Therefore, by identifying an occurrence of such displacement, the crack can be indirectly detected. Here, the identification of the above-described displacement can be carried out with an apparatus that requires a lower cost, as compared with the case of directly identifying the crack. In reality, the apparatus (visual inspection apparatus 18) of lower cost as compared with the SEM is employed in the present embodiment to carry out an inspection for a generation of a crack. Thus, for the semiconductor device 1 having such structure, a highly precise visual inspection can be conducted with lower cost.

According to the present embodiment, a step/crack, which is otherwise difficult to be detected in the conventional visual inspection process, can be detected just after the dicing process. Thus, a generation of a defect can be readily prevented, thereby providing an improved reliability. In particular, the configuration of the present embodiment is very effective in providing an improved reliability for the manufacture of the semiconductor devices including weak low-K film.

Further, an identification of a displacement of the dummy metal via 15 is conducted by the omnifocal photography process from above the semiconductor device 1. In such process, images of the dummy metal via 15 are picking up while moving the camera 19 in Z-direction to move its focus. Since the position corresponding to the focal point of the camera 19 moves by the distance that the dummy metal via 15 is moved, a condition of a growth of a crack in the surface of the substrate can be visually observed in continuous observations.

Further, the dummy metal via 15 is provided in the entire periphery of the region 90 for forming the electric circuit. This allows detecting a crack by observing the dummy metal via 15, even if the crack is generated with any position in the periphery of the region 90 for forming an electric circuit.

Figure 12:
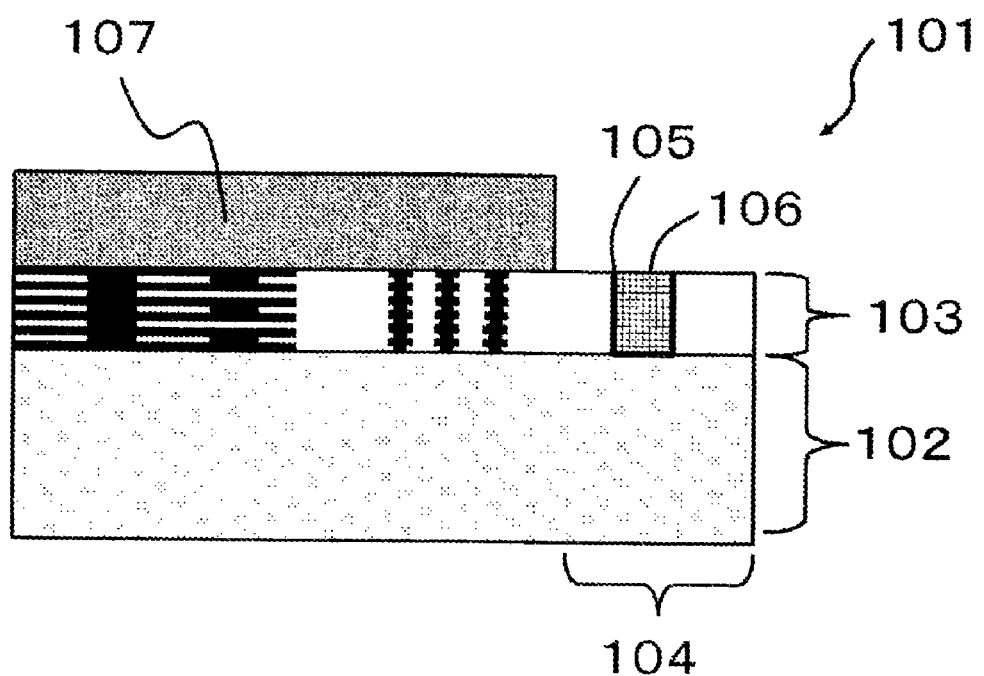
FIG. 12 is a cross-sectional view, illustrating a conventional semiconductor device.

FIG. 12 is a cross-sectional view illustrating a semiconductor device described in Japanese Patent Laid-Open No. 2005-260,059. In a semiconductor device 101, a trench 105 is formed in vicinity of a scribe line 104 in an interconnect layer 103 on a silicon substrate 102. Such trench 105 is filled with a nonmetallic material 106. No polyimide film 107 is provided on the scribe line 104. According to the disclosure of Japanese Patent Laid-Open No. 2005-260,059, it is described that a shock and a crack can be prevented by filling the trench 105 in vicinity of the scribe line 104 with the nonmetallic material 106. However, the semiconductor device 101 having such structure is not suitable for the purpose of detecting a generation of a crack during an experimental production or an evaluation, unlike as the semiconductor device 1 of the present embodiment according to the present invention.

Figure 13:
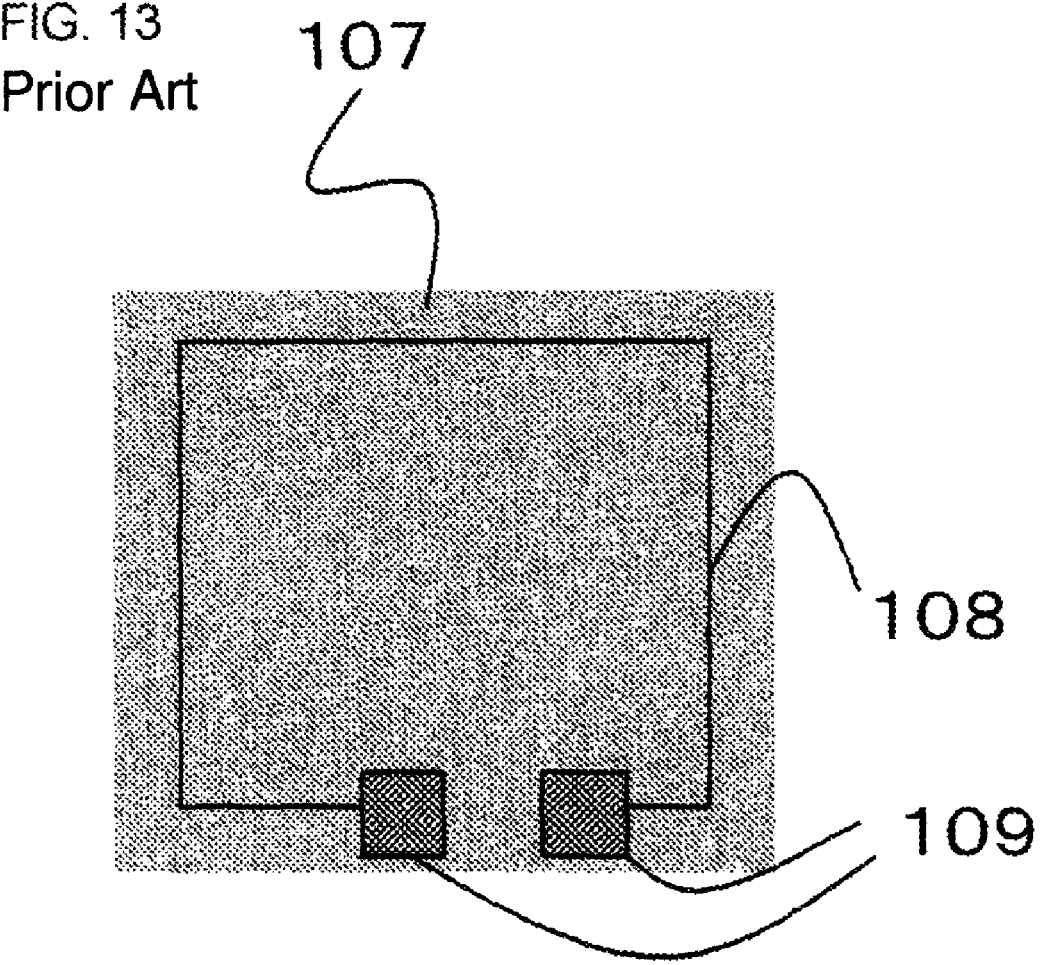
FIG. 13 is a plan view, illustrating a conventional semiconductor device.

FIG. 13 is a plan view, illustrating a semiconductor device described in Japanese Patent Laid-Open No. 2005-277,338. In this semiconductor device, an electrically conducting interconnect 108 and pads 109 are provided along a scribe line. According to Japanese Patent Laid-Open No. 2005-277,338, it is described that a measured value of resistance is changed when an electrically conducting interconnect 108 is damaged by a crack, so that failure chips can be classified by a screening. However, a determination of a failure has been first achieved in the screening process after the assembly of the device is completed for the configuration of such semiconductor device. Thus, there is the fear that a cost is increased by producing too many assemblies. Further, certain time and dates are required from the dicing to the screening processes.

The present invention is not limited to the above-described embodiment, and various modifications thereof may also be employed. The exemplary implementation having the dummy metal via 15 provided in the entire periphery of the region 90 for forming the electric circuit is illustrated in the above-described embodiment. Alternatively, the dummy metal via 15 may also be provided only in a portion of the periphery of the region 90 for forming the electric circuit. For example, the dummy metal via 15 may be formed in the region 90 for forming the electric circuit except corners thereof.

Further, the semiconductor device of the present invention may be in a condition of a wafer (condition before dicing), or may be a condition of chips (condition after dicing).

What is claimed is:

1. A method for inspecting an appearance of a semiconductor device having a region for forming an electric circuit, comprising:

a guard ring, provided in an interconnect layer, and surrounding said region for forming the electric circuit; and at least one dummy metal via, provided in said interconnect layer and located outside of said guard ring, wherein a width of said dummy metal via is smaller than a width of said guard ring in a cross section that is perpendicular to a direction of an elongation of said guard ring, and an area between the region for forming the electric circuit and the guard ring is void of the at least one dummy metal via;

the method for inspecting comprising:

identifying an occurrence of a displacement of said dummy metal via.

2. The method for inspecting the appearance of the semiconductor device as set forth in claim 1, wherein said at least one dummy metal via is provided over an entire peripheral of said region for forming the electric circuit.

3. The method for inspecting the appearance of the semiconductor device as set forth in claim 1, wherein said at least one dummy metal via is composed of aluminum (Al), copper (Cu) or tungsten (W).

4. The method for inspecting the appearance of the semiconductor device as set forth in claim 1, wherein said at least one dummy metal via is provided in a section between the guard ring and scribe lines of the semiconductor device.

5. The method for inspecting the appearance of the semiconductor device as set forth in claim 1, wherein said at least one dummy metal via includes a plurality of dummy metal vias, each formed in a section between the guard ring and scribe lines of the semiconductor device.

6. The method for inspecting the appearance of the semiconductor device as set forth in claim 5, wherein each of the plurality of dummy metal vias is disposed adjacent to each other.

7. The method for inspecting the appearance of the semiconductor device as set forth in claim 1, wherein said identification of the occurrence of the displacement of said dummy metal via is carried out by an omnifocal imaging process from above said semiconductor device.

* * * * *